(12) United States Patent
Godfrey

(10) Patent No.: US 7,833,519 B2
(45) Date of Patent: Nov. 16, 2010

(54) METHOD OF PRE-TREATMENT FOR HAIR COLOURANTS AND BLEACHES

(75) Inventor: Simon Paul Godfrey, Uxbridge (GB)

(73) Assignee: The Procter & Gamble Company, Cincinnati, OH (US)

( * ) Notice: Subject to any disclaimer, the term of this patent is extended or adjusted under 35 U.S.C. 154(b) by 1455 days.

(21) Appl. No.: 11/233,278

(22) Filed: Sep. 22, 2005

(65) Prior Publication Data

US 2006/0064824 A1 Mar. 30, 2006

(30) Foreign Application Priority Data

Sep. 24, 2004 (EP) .................. 04255823

(51) Int. Cl.
*A61Q 5/12* (2006.01)
*A61Q 5/00* (2006.01)

(52) U.S. Cl. .................. 424/70.6; 424/62; 424/70.1

(58) Field of Classification Search .................. None
See application file for complete search history.

(56) References Cited

U.S. PATENT DOCUMENTS 4,217,914 A    8/1980   Jacquet et al.

2003/0121109 A1   7/2003   Devin-Baudoin et al.
2003/0126692 A1   7/2003   Devin-Baudoin et al.

FOREIGN PATENT DOCUMENTS

| EP | 1428497 A | | 6/2004 |
|---|---|---|---|
| EP | 1466581 A | | 10/2004 |
| GB | 2186889 A | | 8/1987 |
| WO | WO-99/26510 A1 | | 6/1999 |
| WO | WO-99/26511 A1 | | 6/1999 |
| WO | WO-99/26596 A1 | | 6/1999 |
| WO | WO 01/17492 | * | 3/2001 |
| WO | WO 01/76545 | * | 10/2001 |
| WO | WO 02/092034 | * | 11/2002 |

* cited by examiner

*Primary Examiner*—Jyothsna A Venkat
(74) *Attorney, Agent, or Firm*—Laura R. Grunzinger; Melissa G. Krasovec

(57) ABSTRACT

The present invention is a method of pre-treating keratinous fibers prior to the application of a hair colorant or bleaching composition comprising the steps of applying a pre-treatment composition to the keratinous fibers said composition comprising at least one conditioning agent, said composition having a viscosity of from 100 Pa cps to 300 Pa, wherein said pre-treatment composition is not rinsed off from the hair prior to the application of said hair coloring or bleaching composition.

4 Claims, No Drawings

METHOD OF PRE-TREATMENT FOR HAIR COLOURANTS AND BLEACHES

FIELD OF THE INVENTION

The present invention relates to a method of pre-treatment of keratinous fibres prior to the application of a bleaching or colorant composition to the fibres.

BACKGROUND OF THE INVENTION

The alteration of the color of keratinous fibers, in particular human hair, by the application of hair dyes is well known. In order to provide the consumer with the hair color and the intensity of color desired, a very complex chemical process is utilized. Non permanent hair colorant formulations typically comprise a non permanent dye such as direct dyes and or pigments which are deposited on to the surface of the hair and are gradually washed out over successive washing cycles. Permanent hair colorant formulations typically comprise oxidative hair dye precursors, which can diffuse into the hair through the cuticle and into the cortex where they can then react with each other and suitable oxidising agents to form the end dye molecules. Due to the large size of these resultant molecules they are unable to readily diffuse out of the hair during subsequent washing with water and/or detergents; hence delivering the consumer-desired permanency of color. The reaction typically takes place in an aggressive environment at approximately pH 9 to 11 in the presence of an alkalizing agent and in the presence of an oxidizing agent. Moreover, the consumer repeats this process regularly in order to maintain the desired hair color shade and the intensity of color and to ensure continual, even coverage of the hair including coverage of new hair growth. Hair bleaching and highlighting compositions further typically utilize a strong oxidizing agent such as hydrogen peroxide and a persulphate salt in order to lighten the hair colour.

However, despite the fact that commercial hair colorant products have been available for many years, the products still exhibit a number of consumer-related deficiencies. The process of applying the hair coloring or bleaching composition to the consumer's hair by the consumers themselves is not a simple process. In particular, the application of hair colorant products is still a relatively time consuming process and it may take the consumer over an hour to mix, apply, wait for the color to develop and remove the product, before even drying and styling. Since for most consumers the hair coloring process is a regular part of their beauty routine it would thus be highly desirable if the time required to dye the hair could be reduced.

Furthermore, the application of the hair colorant or bleach also requires dexterity and patience by the consumer to ensure a satisfactory end result and to prevent any accidental spillages on the consumer's skin, clothing or bathroom furniture. Typically the consumer engages in a complex process to apply the composition to ensure an even color outcome. This is particularly difficult if the hair has been previously colored. In such circumstances the consumer typically firstly applies the composition to the entire root area of the head to cover any regrowth and then subsequently, often by the use of a comb, pulls the composition along the entire length of the hair to the tips to ensure coverage of all of the hair to thus ensure an even end colour result. However the presence of these compositions on the hair typically contributes towards the tangling of the hair, thus making the combing through of the compositions difficult and often even painful. Moreover, the application of the composition through tangled hair may also cause small amounts of the composition to be deposited on the consumer's skin, clothing and bathroom furniture. Consequently, a relatively large amount of the composition is also required in order to satisfactorily cover the entire head of hair.

Many attempts have been made to improve the ease of application of hair colorants on the hair of the consumer. These have typically resided in the development of devices to use in combination with the colorant dispenser, such as comb type applicators as described for example in WO9926510, WO9926511 and WO9926596. However such devices are not only expensive to produce, but also, do not solve the problem of improved ease of application from root to tip of the hair.

It has now been surprisingly found that by the use of a specific pre-treatment method whereby a pre-treatment composition is applied to the hair without rinsing this composition, prior to the application of a hair bleaching or colouring application, allows for the simpler and faster application of the colourant or bleaching composition. In particular, the compositions are easier to apply and reduce the amount of tangled hair generated, associated with the subsequent application of the hair colourant or bleaching composition. Thus this improves the even application of the composition onto the hair. Moreover, the method also requires less colorant or bleaching composition in order to obtain a good color result. Another benefit of the present invention is that the condition of the hair immediately after the bleaching or colouring process is significantly improved, thus negating the requirement of a post bleaching or colourant conditioner application.

The use of pre-treatment compositions for hair coloring compositions is described in the art. US2003/0121109 and US2003/0126692 describe processes for the pre-treatment of keratinous fibers to be colored comprising specified aminosilicones. The pre-treatment compositions may be rinsed off or retained on the fibers prior to colouring and provide improved dye deposition on the fibers and reduce the degradation of the fibers.

SUMMARY OF THE INVENTION

The present invention is a method of pre-treating keratinous fibres prior to the application of a hair colourant or bleaching composition comprising the steps of applying a pre-treatment composition to the keratinous fibres, said composition comprising at least one conditioning agent, said composition having a viscosity of from 100 Pa to 300 Pa (measured accordingly to the test method described herein) wherein, said pre-treatment composition is not rinsed off from the hair prior to the application of said hair colouring or bleaching composition.

DETAILED DESCRIPTION OF THE INVENTION

Except as otherwise noted, amounts represent approximate weight percent of the actual amount of the ingredient, and do not include solvents, fillers or other materials which may be combined with the ingredient in commercially available products, and the amounts include the composition in the form of intended use. Except as otherwise noted, all amounts including part, percentages, and proportions are understood to be modified by the word "about", and amounts are not intended to indicate significant digits.

As used herein, the term "hair" refers to keratinous fibers on a living, e.g. a person, or non-living body, e.g. in a wig, hairpiece, or other aggregation of non-living keratinous fibers. Mammalian, preferably human, hair is preferred. Notably, hair, wool, fur, and other keratinous fibers are suitable substrates for coloring by the compounds and compositions described herein.

According to the present invention the method of pre-treatment comprises applying a pre-treatment composition to the keratinous fibers. The pre-treatment composition of the present invention has a viscosity of from 100 Pa to 300 Pa, preferably from 115 Pa to 285 Pa, more preferably from 130 Pa to 250 Pa cps, most preferably from 160 Pa to 240 Pa, measured according to the test method described herein.

It has been surprisingly found that pre-treatment compositions having such a rheology allow for the improved application of the pre-treatment composition, and further improve the ease of application of a subsequently applied bleaching or colouring composition.

According to the method of the present invention the pre-treatment composition comprises at least one conditioning agent. As used herein, the term "conditioning agent" refers to any agent whose function is to improve at least one cosmetic property of keratin fibers such as hair, for example softness, smoothness, disentangling, feel and static electricity. The at least one conditioning agent may be soluble or insoluble in water.

Conditioning actives suitable for use herein may be selected from: emulsions made from lamellar liquid crystals, cationic polymers, oils and waxes, silicone materials, anionic or non-ionic polymers and mixtures thereof.

Emulsions made from lamellar liquid crystals, suitable for use herein, are formed by the combination of several actives and provide improvement in the cosmetic properties of the composition such as conditioning properties. This arises due to the presence of a combination of fatty materials and an emulsifier to from an emulsion. Emulsifiers for use in the aqueous continuous phase of the emulsion may include an anionic surfactant, cationic surfactant, amphoteric surfactant, water-soluble polymeric surfactant, water-soluble silicone-containing surfactant, non-ionic surfactant having an HLB of greater than about 10, or a surfactant system capable of forming stabilizing liquid crystals. The nonionic surfactant preferably has an HLB of at least 12, and more preferably, an HLB value of at least about 15. Surfactants belonging to these classes are listed in McCutcheon's Emulsifiers and Detergents, North American and International Editions, MC Publishing Co., Glen Rock N.J., pages 235-246 (1993).

The emulsifier for the aqueous phase does not gel the aqueous phase. The emulsifier however may be capable of forming a stabilizing layer of lamellar liquid crystals. For conciseness, the term "liquid crystal structure" as used herein, should be taken to also include gel networks, which are solidified liquid crystals. The surfactant system can be a single surfactant or a blend of surfactants. In some cases, a particular surfactant cannot form a liquid crystal structure alone, but can participate in the formation of liquid crystals in the presence of a second surfactant.

Exemplary classes of surfactants capable of participating in the formation of a liquid crystal, include but are not limited to specific cationic surfactants, anionic surfactants, nonionic surfactants, quaternary ammonium surfactants and lipid surfactants.

Preferred non-ionic surfactants for use in the formation of liquid crystals in the aqueous continuous phase are of the nonionic type and include C16-22 fatty alcohols, and C16-22 fatty alcohol ethoxylates with 1 to 30 ethylene oxide groups and mixtures thereof. Specific examples include cetearyl alcohol, cetyl alcohol, stearyl alcohol, arachidyl alcohol, oleyl alcohol, ceteareth ethoxylates with between 10 and 30 ethylene oxide groups, ceteth ethoxylates with between 10 to 30 ethylene oxide groups, steareth ethoxylates with between 10 and 30 ethoxylates, and combinations thereof. Preferably, C16-22 fatty alcohols are used in combination with C16-22 fatty alcohol ethoxylates at a ratio of between 10:1 to 0.5:1, more preferably between 6:1 and 1:1, and most preferably between 5:1 and 1.5:1.

Preferred cationic surfactants contain quaternary ammonium compounds of formula: [R18R19R20R21N]+X—, where R18 is an alkyl or alkenyl group having from about 8 to 22 carbon atoms, R19 and R20 are both independently either an alkyl or alkenyl group having from about 8 to 22 carbon atoms or alkyl or hydroxyalkyl group having from about 1 to 4 carbon atoms, R21 is an alkyl or hydroxyalkyl group having from about 1 to 4 carbon atoms, and X— is a salt forming anion (e.g. chloride, bromide, acetate, alkylsulfate).

Advantageously, in order to facilitate formation of liquid crystals, the surfactant system may also comprise amidoamines of the following general formula: $R22CONH(CH_2)mN(R23)_2$, wherein R22 is a residue of C8 to C24 fatty acids, R23 is a C1 to C4 alkyl, and m is an integer from 1 to 4. Preferred amidoamine useful in the present invention includes stearamidopropyldimethylamine, stearamidopropyldiethylamine, stearamidoethyl-diethylamine, stearamidoethyldimethylaamine, palmitamidopropyldimethylaamine, palmitamidopropyldiethylamine, palmitamidoethyl-diethylamine, palmitamido-ethyldimethylamine, behenamidopropyldimethylamine, behenamido-propyldiethylamine, behenamidoethyl-diethylamine, behenamidoethyldimethylamine, arachidamidopropyldimethylamine, arachidamido-propyidiethylamine, arachidamidoethyl-diethylamine, arachidamidoethyl-dimethylamine, and mixtures thereof; more preferably stearamido-propyidimethylamine, stearamidoethyidiethylamine, and mixtures thereof.

More advantageously, the amidoamines are partially quaternized with acids selected from the group consisting of L-glutamic acid, lactic acid, hydrochloric acid, malic acid, succinic acid, acetic acid, fumaric acid, L-glutamicio acid hydrochloride, tartaric acid, and mixtures thereof; preferably L-glutamic acid, lactic acid, hydrochloric acid, and mixtures thereof. Preferably, the mole ratio of amidoamine to acid is from about 1:0.3 to about 1:1, more preferably from about 1:0.5 to about 1:0.

Cationic polymers suitable for use as conditioning agents according to the method of the present invention may be chosen from those know in the art as improving at least one cosmetic properties of keratin fibres treated with a cosmetic composition. Cationic polymers can be chosen from those comprising units of at least one amine group chosen from primary, secondary, tertiary and quaternary amine groups that may either form part of the main polymer chain, or be borne by a side substituent that is directly attached to the main polymer chain. Such cationic polymers generally have a number average molecular mass ranging from 500 to $5 \times 10^6$, or more preferably from 1000 to $3 \times 10^6$. Polymers of the polyamine, polyamino amide and polyquaternary ammonium type that may be used include but are not limited to:

1) Homopolymers and copolymers derived from acrylic or methacrylic esters or amides. Copolymers of these polymers can also comprise at least one unit derived from comonomers which may be chosen from the family of acrylamides, methacrylamides, diacetone acylamides, acrylamides and methacrylicamides substituted on the nitrogen with at least one group chosen from lower (C1-C4) alkyls, acrylic and methacrylic acids and esters thereof, vinylactams such as vinlypyrrolidone and vinylcaprolactam, and vinyl esters. Examples of such polymers include:

Copolymers of acrylamide and of methacryloyloxyethyltrimethylammonium methosulfate, examples of which include polymers known via the INCI nomenclature as Polyquaternium-5, such as the products sold under the names Reten 210, Reten 220, Reten 230, Reten 240, Reten 1104, Reten 1105, Reten 1006 by the company Hercules and Merquat 5, Merquat 5 SF by the company Nalco.

Copolymers of vinylpyrrolidone and dimethylaminopropyl methacrylamide, examples of which include polymers known via the INCI nomenclature as Polyquaternium-28, such as the products sold under the name Gafquat HS-100 by the company International Speciality Products (ISP).

Copolymers of vinyl pyrrolidone and dialkyaminoalkyl acrylates or methactylates, examples of which include polymers known via the INCI nomenclature as Polquaternium-11, such as the products sold under the name Gafquat 440, Gafquat 734, Gafquat 755, Gafquat 755N by the company International Speciality Products (ISP), and Luviquat PQ11 PM by the company BASF and Polyquat-11 SL by the company Sino Lion.

Copolymers vinylpyrrolidone, dimethylaminopropyl methacrylamide and methacryloylaminopropyl lauryldimonium chloride, examples of which include polymers known via the INCI nomenclature as polyquaternium-55, such as the products sold under the name Styleze W-20 by the company International Speciality Products (ISP).

Copolymers of acrylic acid, acrylamide and methacrylamidopropyltrimonium chloride, examples of which include polymers known via the INCI nomenclature as Polyquaternium-53, such as the products sold under the name Merquat 2003 by the company Nalco.

Copolymers of dimethyaminopropylacrylate (DMAPA), acrylic acid and acrylonitrogens and diethyl sulfate, examples of which include polymers known via the INCI nomenclature as Polyquaternium-31, such as the products sold under the name Hypan QT100 by the company Lipo.

Copolymers of acrylamide, acrylamidopropyltrimonium chloride, 2-amidopropylacrylamide sulfonate, and dimethyaminopropylacrylate (DMAPA), examples of which include polymers known via the INCI nomenclature as polyquaternium-43, such as the products sold under the name Bozequat 4000 by the company Clairant.

Copolymers of acrylic acid, methylacrylate and methacrylamidopropyltrimonium chloride, examples of which include polymers known via the INCI nomenclature as Polyquaternium-47, such as the products sold under the name Merquat 2001 and Merquat 2001N sold commercially by Nalco.

Copolymers of methacryloyl ethyl betaine, 2-hydroxyethyl methacrylate and methacryloyl ethyl trimethyl ammonium chloride, examples of which include polymers known via the INCI nomenclature as Polyquaternium-48, such as the products sold under the name Plascize L-450 by the company Goo Chemcial.

Copolymers of acrylic acid diallyl dimethyl ammonium chloride and acrylamide, examples of which include polymers known via the INCI nomenclature as polyquaternium 39, such as the products sold under the name Merquat 3330 and Merquat 3331 by the company Nalco.

Further examples include copolymers of methacrylamide methacrylamidopropyltrimonium and methacryloylethyltrimethyl ammonium chloride and their derivatives, either homo or copolymerised with other monomers, examples of which include polymers known via the INCI nomenclature as: Polyquaternium-8, Polyquaternium-9, Polyquaternium-12, Polyquaternium-13 Polyquaternium-14, Polyquaternium-15, such as the products sold under the name Rohagit KF 720 F by the company Rohm, Polyquaternium-30, such as the products sold under the name Mexomere PX by the company Chimex, Polyquaternium-33, Polyquaternium-35, Polyquaternium-36, such as the products sold under the name Plex 3074 L by the company Rhon, Polyquaternium 45, such as the products sold under the name Plex 3073L by the company Rohn, Polyquaternium 49, such as the products sold under the name Plascize L-440 by the company Goo Chemicals, Polyquaternium 50 such as the products sold under the name Plascize L-441 by the company Goo Chemicals, Polyquaternium-52.

2) Cationic polysaccharides, such as cationic celluloses and cationic galactomannan gums. Among the cationic polysaccharides that maybe mentioned, for example, are cellulose ether derivatives comprising quaternary ammonium groups and cationic cellulose copolymers or cellulose derivatives grafted with a water-soluble quaternary ammonium monomer and cationic galactomannan gums. Examples include but are not limited to:

Copolymers of hydroxyethylcelluloses and diallyldimethyl ammonium chlorides, examples of which include polymers known via the INCI nomenclature as Polyquaternium-4, such as the products sold under the name Celquat L 200 and Celquat H 100 by the company National Starch.

Copolymers of hydroxyethylcelluloses and a trimethyl ammonium substituted epoxide, examples of which include polymers known via the INCI nomenclature as Polyquaternium-10, such as the products sold under the name AEC Polyquaternium-10 by the company A&E Connock, Catinal C-100 Catinal HC-35 Catinal HC-100 Catinal HC-200 Catinal LC-100 Catinal LC-200 by the company Toho, Celquat SC-240C Celquat SC-230M, by the company National Starch, Dekaquat 400, Dekaquat 3000 by the company Dekker, Leogard GP by the company Akzo Nobel, RITA Polyquta 400 RITA, Polyquta 3000 by the company RITA, UCARE Polymer JR-125 UCARE Polymer JR-400 UCARE Polymer JR-30M UCARE Polymer LK UCARE Polymer LR 400 UCARE Polymer LR 30M by the company Amerchol.

Copolymers of hydroxyethylcelluloses and lauryl dimethyl ammonium substituted epoxides, examples of which include polymers known via the INCI nomenclature as Polyquaternium-24, such as the products sold under the name Quatrisoft polymer LM-200 by the company Amerchol.

Derivatives of Hydroxypropyl Guar, examples of which include polymers known via the INCI nomenclature as Guar Hydroxypropyltrimonium Chloride, such as the products sold under the name Catinal CG-100, Catinal CG-200 by the company Toho, Cosmedia Guar C-261N, Cosmedia Guar C-261N, Cosmedia Guar C-261N by the company Cognis, DiaGum P 5070 by the company Freedom Chemical Diamalt, N-Hance Cationic Guar by the company Hercules/Aqualon, Hi-Care 1000, Jaguar C-17, Jaguar C-2000, Jaguar C-13S, Jaguar C-14S, Jaguar Excel by the company Rhodia, Kiprogum CW, Kiprogum NGK by the company Nippon Starch.

Hydroxypropyl derivatives of Guar Hydroxypropyltrimonium Chloride, examples of which include polymers known via the INCI nomenclature as Hydroxypropyl Guar Hydroxypropyltrimonium Chloride, such as the products sold under the name Jagaur C-162 by the company Rhodia.

3) Polyamino amide derivatives resulting from the condensation of polyalkylene polyamines with polycarboxylic acids followed by alkylation with difunctional agents. Among the derivatives, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Non-limiting examples of such derivatives include adipic acid/epxoypropyl/diethylenetriamine.

5) Cyclopolymers of dialkdiallylamine or of dialkyldiallyammonium, among which polymers mention may be made of:

Dimethyldiallyammonium chloride polymers, examples of which include polymers known via the INCI nomenclature as Polyquaternium-6, such as the products sold under the name Merquat 100 by the company Nalco, Mirapol 100 by the company Rhodia, Rheocare CC6 by the company Cosmetic Rheologies, AEC polyquaternium-6 by the company A&E Connock, Agequat 400 by the company CPS, Conditioner P6 by the company 3V Inc., Flocare C106 by the company SNF, Genamin PDAC by the company Clariant, Mackernium 006 by the company McIntyre.

Copolymers of acrylamides and dimethyldiallylammonium chlorides monomers, examples of which include polymers known via the INCI nomenclature as Polyquaternium-7, such as the products sold under the name AEC Polyquaternium-7 by the company A&E Connock, Agequat-5008, Agequat C-505 by the company CPS, Conditioner P7 by the company 3V Inc. Flocare C 107 by the company SNF Mackernium 007, Mackernium 007S by the company McIntyre, ME Polymer 09W by the company Toho, Merquat 550, Merquat 2200, Merquat S by the company Nalco, Mirapol 550 by the company Rhodia, Rheocare CC7, Rheocare CCP7 by the company Cosmetic Rheologies, Salcare HSP-7, Salcare SC10, Salcare Super 7 by the company Ciba.

Copolymers of dimethyldiallylammoniumchlorides and acrylic acids, examples of which include polymers known via the INCI nomenclature as polyquaternary-22, such as the products sold under the name Merquat 280 and Merquat 295 by the company Nalco.

6) Quaternary diammonium polymers comprising repeat units corresponding to [—N+(R1)(R2)-A1—N+(R3)(R4)-B1-][2X—], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other than nitrogen, or R1, R2, R3 and R4, are chosen from linear or branched C1-C6 alkyl radicals substituted with at least one group chosen from nitrile, ester, acyl and amide groups and groups of —CO—O—R5-D and —CO—NH—R5-D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X— is an anion derived from inorganic and organic acids. D is chosen from a glycol residue, a bis-secondary diamine residue, a bis-primary diamine residue or a ureylene group. Examples include polymers known via the INCI nomenclature as Hexadimethrine chloride, where R1, R2, R3 and R4 are each methyl radicals, A1 is (CH2)3 and B1 is (CH2)6 and X=Cl. Further examples of which include polymers known via the INCI nomenclature as polyquaternium-34 where R1 and R2 are ethyl radicals and R3 and R4 are methyl radicals and A1 is (CH2)3 and B1 is (CH2)3 and X=Br, such as the products sold under the name Mexomere PAX by the company Chimax.

7) Polyquaternary ammonium polymers comprising repeating units of formula [—N+(R6)(R7)—(CH2)r—NH—CO—(CH2)q—(CO)t—NH—(CH2)s—N+(R8)(R9)—A—][2X—], in which R6, R7, R8 and R9 which may be identical or different, are chosen from a hydrogen atom and a methyl, ethyl, propyl, hydroxyethyl, hydroxypropyl, and —CH2CH2(OCH2CH2)pOH radicals, wherein p is equal to 0 or an integer ranging from 1 to 6, wherein R6, R7, R8 and R9 do not all simultaneously represent a hydrogen atom. R and s which maybe identical or different are each an integer ranging from 1 to 6, q is equal to 0 or an integer ranging from 1 to 34 and X— is anion such as a halide. T is an integer chosen to be equal to 0 or 1. A is chosen from divalent radicals such as —CH2—CH2—O—CH2—CH2—. Examples of which include Polymers known via the INCI nomenclature as polyquaternium-2, where r=s=3, q=0, t=0, R6, R7, R8 and R9 are methyl groups, and A is —CH2—CH2—O—CH2—CH2, such as the products sold under the name Ethpol PQ-2 from Ethox and Mirapol A-15 by the company Rhodia.

Polymers known via the INCI nomenclature as polyquaternium-17 where r=s=3, q=4, t=1 R6, R7, R8 and R9 are methyl groups, and A is —CH2—CH2—O—CH2—CH2. Polymers known via the INCI nomenclature as Polyquaternium 18, where r=s=3, q=7, t=1 R6, R7, R8 and R9 are methyl groups, and A is —CH2—CH2—O—CH2—CH2 Polymers known via the INCI nomenclature as the block copolymer formed by the reaction of Polyquaternium-2 with Polyquaternium-17, known as Polyquaternium 27, such as the products sold under the name Mirapol 175 by the company Rhodia.

8) Copolymers of vinylpyrrolidones and of vinylimidazoles and optionally vinylcaprolactums, examples of which include polymers known via the INCI nomenclature as Polyquaternary-16 formed from methylvinylimidazolium chlorides and vinylpyrrolidones, such as the products sold under the name Luviquat FC370, Luviquat FC550, Luviquat FC905, Luviquat HM-552 by the company BASF. Or copolymers of vinylcaprolactams and vinylpyrrolidones with methylvinylimidazolium methosulfates, examples of which include polymers known via the INCI nomenclature as Polyquaternium-46, such as the products sold under the name Luviquat Hold by the company BASF. Or copolymers of vinylpyrrolidones and quaternized imidazolines, examples of which include polymers known via the INCI nomenclature poylquaterary 44, such as the products sold under the name Luviquat Care by the company BASF 9) Polyamines such as the product Polyquart H sold by Cognis under the reference name polyethylene glycol (15) tallow polyamine in the CTFA dictionary.

10) Cross linked methacryloyloxy(C1-C4)alkyltri(C1-C4)alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, examples of which include polymers known via the INCI nomenclature as Polyquaternium-37, such as the products sold under the name Synthalen, CN Synthalen CR, Synthalen CU, sold by 3V sigma, or as a dispersion in another media such as the products sold under the name Salcare SC95 and Salcare SC96 by the company Ciba or Rheocare CTH(E) by the company Cosmetic Rheologies. Or in another example of which include polymers known via the INCI nomenclature as Polyquaternium-32, or when sold as a dispersion in mineral oil such as the products sold under the name Salcare SC92 by the company Ciba.

11) Further examples of cationic polymers include polymers known via the INCI nomenclature as Polyquaternium 51, such as the products sold under the name Lipidure-PMB by the company NOF, via the INCI nomenclature as Polyquaternium 54, such as the products sold under the name Qualty-Hy by the company Mitsui, and via the INCI nomenclature as Polyquaternium 56 such as the products sold under the name Hairrol UC-4 by the company Sanyo chemicals.

12) Silicone polymers comprising cationic groups and/or groups which may be ionised into cationic groups. For example: cationic silicones of the general formula (R10-N+(CH3)2)-R11—(Si(CH3)2-O)x-R11—(N+(CH3)2)—R10), where R10 is an alkyl derived from coconut oil, and R11 is (CH2CHOCH2O(CH2)3 and x is a number between 20 and 2000, examples of which include polymers known by the INCI nomenclature as Quaternium 80, such as the products sold under the name as Abil Quat 3272 and Abil Quat 3474 sold commercially by Goldschmidt.

Silicones containing groups which may be ionised into cationic groups, for example aminosilicones containing at least 10 repeating siloxane —Si(CH3)2—O) units within the polymer chain, with either terminal, graft or a mixture of terminal and graft aminofunctional groups. Example functional groups are not limited to aminoethylaminopropyl, aminoethylaminoisobutly, aminopropyl. In the case of graft polymers, the terminal siloxane units can either be (CH3)3Si—O or R12(CH3)2Si—O, where R12 can be either OH or OR13, where R13 is a C1-C8 alky group, or a mixture of both functional terminal groups. These silicones are also available as preformed emulsions. Polymer with terminal siloxane units of (CH3)3Si—O examples of which include polymers known by the INCI nomenclature as trimethylsilylamodimethicone, such as the products sold under the name as DC-2-8566, DC 7224 and DC-2-8220 sold commercially by Dow Corning and SF1708 and SM 2125 sold commercially by GE Silicones and Wacker Belsil ADM 653 sold commercially by Wacker silicones. Further examples include polymers with terminal siloxane units of (R12O)(CH3)2Si—O where R12 can be either OH or OR13, where R13 is a C1-C8 alky group, or a mixture of both functional terminal groups, known by the INCI nomenclature as amodimethicone, such as the products sold under the name as Wacker Belsil ADM 1100, Wacker Belsil ADM 1600, Wacker Belsil ADM 652, Wacker Belsil ADM 6057E, Wacker Belsil ADM 8020 sold commercial by Wacker Silicones, DC929, DC939, DC949 and DC AP 6087 sold commercially by Dow Corning and SM2059 sold commercially by GE silicones. Silicones containing groups which may be ionised into cationic groups—for example silicones containing at least 10 repeating siloxane —(Si(CH3)2—O) units within the polymer chain, with either terminal, graft or a mixture of terminal and graft aminofunctional groups, together with additional functional groups. Additional functional groups can include polyoxyalkylene, the reaction product of amines and carbinols, alky chains. For example products know by the INCI nomenclature as methoxy PEG/PPG-7/3 Aminopropyl Dimethicone, such as the product sold under the name of Abil Soft AF100 sold commercially by Degussa. For example products know by the INCI nomenclature as Bis (C13-15 Alkoxy) PG Amodimethicone, such as the product sold under the name of DC 8500 sold commercially by Dow Corning.

Examples of oils suitable for use as conditioning agents in the method of the present invention include both animal and plant oils, and are for example, chosen from sunflower oil, corn oil, soybean oil, avocado oil, jojoba oil, marrow oil, grape seed oil, sesame oil, hazelnut oil, fish oils, glyceryl tricaprocaprylate, and plant and animal oils of formula $R_9COOR_{10}$ in which R9 is chosen from higher fatty acid residues containing from 7 to 29 carbon atoms and $R_{10}$ is chosen from linear and branched hydrocarbon-based chains containing from 3 to 30 carbon atoms, such as alkyl and alkenyl, for example, purcellin oil and liquid jojoba wax.

The waxes suitable for use herein are natural (animal or plant) or synthetic substances that are solid at room temperature (20°-25° C.). They are insoluble in water, soluble in oils and are capable of forming a water-repellent film. The waxes are chosen, for example, from carnauba wax, candelilla wax, alfalfa wax, paraffin wax, ozokerite, plant waxes such as olive tree wax, rice wax, hydrogenated jojoba wax and absolute waxes of flowers such as the essential wax of blackcurrant flower sold by the company Bertin (France), animal waxes such as beeswaxes, and modified beeswaxes (cerabellina). Other waxes or waxy starting materials, which can be used, include, for example, marine waxes such as the product sold by the company Sophim under the reference M82, and polyethylene waxes and polyolefins in general.

Silicones suitable for use herein are chosen, for example, from polyorganosiloxanes that can be insoluble in the composition and may be in the form of oils, waxes, resins or gums. The volatile organopolysiloxanes are, for example, chosen from those having a boiling point ranging from 60° C. to 260° C., and, further, for example, are chosen from cyclic silicones comprising from 3 to 7 silicon atoms, such as 4 to 5 silicon atoms. These cyclic silicones are, for example, octamethylcyclotetrasiloxane sold, for example, under the name "Volatile Silicone 7207" by Union Carbide or "Silbione 70045 V 2" by Rhodia Chimie, decamethylcyclopentasiloxane sold under the name "Volatile Silicone 7158" by Union Carbide, and "Silbione 70045 V 5" by Rhodia Chimie, and mixtures thereof.

Non-volatile silicones, and, for example, polyalkylsiloxanes, polyarylsiloxanes, polyalkylarylsiloxanes, silicone gums and resins, polyorganosiloxanes modified with organofunctional groups, and mixtures thereof, may also be used. These silicones are further, for example, chosen from polyalkylsiloxanes, among which mention may be made, for example, of polydimethylsiloxanes comprising trimethylsilyl end groups having a viscosity of from $5 \times 10^{-6}$ to 2.5 m$^2$/s at 25° C. and such as from $1 \times 10^{-5}$ to 1 m$^2$/s. Mention may also be made, for example, of polydimethylsiloxanes comprising dimethylsilanol end groups (Dimethiconol according to the CTFA name) such as the oils of the 48 series from the company Rhodia Chimie. The silicone gums that can be used are, for example, chosen from polydiorganosiloxanes having the number-average molecular masses ranging from 200 000 to 1 000 000, used alone or as a mixture in at least one solvent. This solvent can, for example, be chosen from volatile silicones, polydimethylsiloxane (PDMS) oils, polyphenylmethylsiloxane (PPMS) oils, isoparaffins, polyisobutylenes, methylene chloride, pentane, dodecane and tridecanes, and mixtures thereof.

The organopolysiloxane resins that can be used are crosslinked siloxane systems comprising at least one of the following units: $R_2SiO_{2/2}$, $R_3SiO_{1/2}$, $RSiO_{3/2}$ and $SiO_{4/2}$ wherein R is chosen from hydrocarbon-based groups comprising from 1 to 16 carbon atoms and phenyl groups. Among these products, examples include the ones in which R is chosen from $C_1$-$C_4$ lower alkyl radicals, such as methyl, and a phenyl radical.

The organomodified silicones are silicones as defined above and comprising in their structure at least one organo-functional group attached via a hydrocarbon-based radical. Among the organomodified silicones mention may be made, for example, of polyorganosiloxanes comprising at least one group chosen from:

A) polyethylenoxy and polypropylenoxy groups optionally containing $C_6$-$C_{24}$ alkyl groups, such as the products known as dimethicone copolyol sold by the company Dow Corning under the name DC 1248 and the $(C_{1-2})$alkylmethicone copolyol sold by the company Dow Corning under the name Q2 5200;

B) alkoxylated groups such as the product sold under the name "Silicone Copolymer F-755" by SWS Silicones and Abil Wax 2428, 2434 and 2440 by the company Goldschmidt; and C) anionic groups of carboxylic type, such as the products described in patent EP 186 507 from the company Chisso Corporation, and ionic groups of alkylcarboxylic type, such as those present in the product X-22-3701 E from the company Shin-Etsu; 2-hydroxyalkyl sulphonate; 2-hydroxyalkyl thiosulphate such as the products sold by the company Goldschmidt under the names "Abil S201" and "Abil S255";

Polymers suitable as conditioning agents according to the present invention include anionic and nonionic polymers, which may be water-soluble or water insoluble.

Suitable anionic polymers include polymers comprising at least one group derived from carboxylic acid, sulphonic acid or phosphoric acid and such as those having a weight-average molecular weight ranging from 500 to 5,000,000, determined, for example, by gel permeation chromatography.

Suitable nonionic polymers include for example, from the following polymers: vinylpyrrolidone homopolymers; copolymers of vinylpyrrolidone and vinyl acetate; polyalkyloxazolines such as the polyethyloxazolines sold by the company Dow Chemical under the names "Peox 50 000", "Peox 200 000" and "Peox 500 000"; vinyl acetate homopolymers, such as the product sold under the name "Appretan EM" by the company Hoechst, and the product sold under the name "Rhodopas A 012" by the company Rhodia Chimie; copolymers of vinyl acetate and acrylic ester, such as the product sold under the name "Rhodopas AD 310" by Rhodia Chimie; copolymers of vinyl acetate and ethylene, such as the product sold under the name "Appretan TV" by the company Hoechst; copolymers of vinyl acetate and maleic ester, for example of dibutyl maleate, such as the product sold under the name "Appretan MB Extra" by the company Hoechst; copolymers of polyethylene and maleic anhydride; alkyl acrylate homopolymers and alkyl methacrylate homopolymers, such as the product sold under the name "Micropearl RQ 750" by the company Matsumoto or the product sold under the name "Luhydran A 848 S" by the company BASF; acrylic ester copolymers such as copolymers of alkyl acrylates and alkyl methacrylates, such as the products sold by the company Rohm & Haas under the names "Primal AC-261 K" and "Eudragit NE 30 D", by the company BASF under the names "Acronal 601", "Luhydran LR 8833" and 8845, and by the company Hoechst under the names "Appretan N 9213" or N 9212; copolymers of acrylonitrile and a nonionic monomer chosen, for example, from butadiene and alkyl (meth)acrylates; mention may be made of the products sold under the names "Nipol LX 531 B" by the company Nippon Zeon and those sold under the name "CJ 0601 B" by the company Rohm & Haas; polyurethanes, such as the products sold under the names "Acrysol RM 1020" and "Acrysol RM 2020" by the company Rohm & Haas, and the products "Uraflex XP 401 UZ" and "Uraflex XP 402 UZ" by the company DSM Resins; copolymers of alkyl acrylate and urethane, such as the product "8538-33" by the company National Starch; polyamides, such as the product "Estapor LO 11" sold by the company Rhodia Chimie; and unmodified and chemically modified nonionic guar gums.

The pre-treatment compositions preferably comprise a conditioning agent comprising an emulsion made from lamellar liquid crystals, more preferably a fatty alcohol and surfactant emulsion.

The pre-treatment composition comprises from 0.2% to 20% preferably from 1.0% to 15%, more preferably from 5% to 15% of said conditioning agents. The pre-treatment compositions for use herein also preferably have a pH of from 3 to 7 more preferably from pH 4 and pH 6.

The pre-treatment composition may further comprise additional adjuncts, which are selected so as not to eliminate or substantially reduce the performance or shelf stability of the composition. The additional ingredients may include, for example dyes and coloring agents, fragrances; anionic, cationic, non-ionic, amphoteric or zwitterionic surfactants; buffers, masking fragrances, dispersing agents, stabilizers, cationic polymers, perfumes, non-ionic polymers, anionic polymers, complex coacervates, complex coacervate capsules, metal salts, lewis acids, buffering agents, particulate thickeners, polymeric thickeners, wax thickeners, oils, emollients, humectants, moisturizers, pearlescents, opacifiers, enzymes, suspending agents, antimicrobials, preservatives, proteins, herb and plant extracts, bleach, peroxide, polyols, silicones, solvents, antibodies, pH adjusting agents including pH buffers, viscosity modifiers, preservatives, viscosity enhancers, gelling agents, chelators, oxidising agents, reducing agents, UV filters, emulsifying agents, antioxidants, moisturizing and conditioning agents, and other common adjuvants well known to those skilled in the art.

Method of Use

The pre-treatment compositions of the present invention may be sold separately or preferably as part of a bleaching or coloring kit described herein below, provided as a further individually packaged component in a separate container.

Oxidative hair dye compositions are usually sold in kits comprising, in individually packaged components such as separate containers, a dye component (also called "dye cream" for emulsions or "dye liquid" for solutions) comprising the oxidative dye, precursors and alkalizing agent which is typically ammonia in a suitable carrier and; a hydrogen peroxide component (also called "hydrogen peroxide cream" for emulsions or "hydrogen peroxide liquid" for solutions) comprising the oxidizing agent (usually hydrogen peroxide). The consumer mixes the dye component and hydrogen peroxide component together immediately before use and applies it onto the hair. Optionally, these kits may comprise a post treatment conditioner.

Similarly, bleaching compositions are also usually sold as a kit comprising two or three individually packaged components typically in two or three separate containers. The first component comprises the ammonium ion source (e.g. ammonia), the second component comprises the oxidizing agent and the third (optional) component comprises a second oxidizing agent. The bleaching compositions are obtained by mixing the above-mentioned compositions immediately before use. Optionally, these bleaching kits may comprise a post treatment conditioner.

Non oxidative coloring compositions typically are also sold as a kit and contain one or two individually packaged components, the first containing the colorant composition and optionally the second containing a post treatment conditioner.

When present in the colorant compositions and bleaching compositions, the optional conditioning agent can be provided in a separate container. In the latter case, all the compositions can be mixed immediately before use and applied together, or the content of the additional container can be applied (after an optional rinse step) as a post-treatment immediately after the colorant composition or bleaching composition resulting from the mixture of the other containers.

The hair coloring or bleaching compositions of such kits will typically comprise at least one source of an oxidizing agent. Preferred oxidizing agents for use herein are water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilisation and decolorisation of the melanin (bleaching) and accelerate the oxidation of the oxidative dye precursors (oxidative dyeing) in the hair shaft.

Any oxidizing agent known in the art may be utilized. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and or peroxidases may also be used. Mixtures of two or more such oxidizing agents can also be used if desired. The oxidizing agents may be provided in aqueous solution or as a powder which is dissolved prior to use. Preferred for use in the compositions according to the present invention are hydrogen peroxide, percarbonate, persulphates and combinations thereof. The hair coloring or bleaching compositions comprise from about 0.1% to about 15% by weight, preferably from about 1% to about 10% by weight, and most preferably from about 2% to about 7% by weight of an oxidizing agent.

Another preferred oxidizing agent for use herein is a source of peroxymonocarbonate ions. Preferably such a source is formed in situ from a source of hydrogen peroxide and a hydrogen carbonate ion source. Such an oxidizing agent has been found to be particularly effective at a pH of up to and including 9.5, preferably from 7.5 to 9.5 more preferably from 8.4 to 9.5 and most preferably at about pH 9. Moreover, this system is also particularly effective in combination with a source of ammonia or ammonium ions. It has been found that this oxidizing agent can deliver improvements to the desired hair color results particularly with regard to the delivery of high lift, whilst considerably reducing the odour, skin and scalp irritation and damage to the hair fibers.

Accordingly, any source of these ions may be utilized. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Preferred sources of carbonate ions, carbamate and hydrocarbonate ions are sodium hydrogen carbonate, potassium hydrogen carbonate, ammonium carbamate, and mixtures thereof.

The hair coloring or bleaching compositions comprise from about 0.1% to about 15% by weight, preferably from about 1% to about 10% by weight, and most preferably from about 1% to about 8% by weight of a hydrogencarbonate ion and from about 0.1% to about 10% by weight, preferably from about 1% to about 7% by weight, and most preferably from about 2% to about 5% by weight of a source of hydrogen peroxide.

The hair coloring or bleaching compositions may further comprise additional ingredients which include, but are not limited to; alkalizing agents, surfactants, hair dyeing agents such as oxidative dye precursors, non-oxidative pre-formed dyes, thickeners and/or rheology modifiers, opacifiers such as mica, solvents, enzymes, surfactants, conditioning agents, carriers, antioxidants, stabilizers, chelants, perming actives, perfume, reducing agents, hair swelling agents and/or polymers. Some of these additional components are detailed hereafter.

In particular, the hair coloring or bleaching composition may optionally comprise at least one source of alkalizing agent, preferably a source of ammonium ions and or ammonia. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium carbonate, ammonium hydrogen carbonate, ammonium carbamate, ammonia and mixtures thereof. The compositions of the present invention may comprise from about 0.1% to about 10% by weight, preferably from about 0.5% to about 5%, most preferably from about 1% to about 3% of an alkalizing agent, preferably ammonium ions. Preferably, if present, the ammonium ions and carbonate ions are present in the composition at a weight ratio of from 3:1 to 1:10, preferably 2:1 to 1:5.

Preferably, the hair coloring compositions have a pH of from about 11 to about 7, preferably from about 9.5 to about 7.5, more preferably from about 9.5 to about 8.4 and most preferably from about 9.4 to about 8.5 and even more preferably about pH 9.0. The pH of the compositions can be determined by using either a Mettler Toledo MP220 or a MP225 pH equipment, fitted with a standard laboratory pH electrode. The equipment is calibrated before each use using standard calibration buffers and using standard calibration procedure.

Preferably, hair coloring compositions comprise but are not limited to oxidative dyeing compositions. Such compositions comprise oxidative hair dye precursors also known as primary intermediates and couplers that will deliver a variety of hair colors to the hair. These small molecules are activated by the oxidizing agent and react with further molecules to form a larger colored complex in the hair shaft.

These compounds are well known in the art, and include aromatic diamines, aminophenols, aromaticdiols and their derivatives. A representative but not exhaustive list of oxidation dye precursor can be found in Sagarin, "Cosmetic Science and Technology", "Interscience, Special Edn. Vol. 2 pages 308 to 310). The hair coloring compositions may also include non oxidative hair dyes. i.e. direct dyes which may be used alone or in combination with the above described oxidative dyes. Suitable direct dyes include azo or anthraquinone dyes and nitro derivatives of the benzene series and or melanin precursors and mixtures thereof.

The hair coloring compositions will generally comprise from about 0.001% to about 10% of dyes. For example compositions providing low intensity dyeing such as natural blonde to light brown hair shades generally comprise from about 0.001% to about 5%, preferably from about 0.1% to about 2%, more preferably from about 0.2% to about 1% by weight of dyeing composition of precursors and couplers. Darker shades such as browns and black typically comprise from 0.001% to about 10% by weight, preferably from about 0.05% to about 7% by weight, more preferably from about 1% to about 5% of precursors and couplers.

The hair coloring or bleaching compositions may also comprise a source of radical scavenger. As used herein the term radical scavenger refers to a species that can react with a radical, preferably carbonate radical to convert the radical by a series of fast reactions to a less reactive species.

Suitable radical scavengers for use herein include compounds according to the general formula:

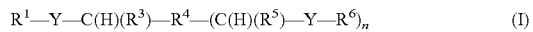

$$R^1-Y-C(H)(R^3)-R^4-(C(H)(R^5)-Y-R^6)_n \qquad (I)$$

wherein Y is $NR^2$, O, or S, preferably $NR^2$, n is 0 to 2, and wherein $R^4$ is monovalent or divalent and is selected from: (a) substituted or unsubstituted, straight or branched, alkyl, mono- or poly-unsaturated alkyl, heteroalkyl, aliphatic, heteroaliphatic, or heteroolefinic systems, (b) substituted or unsubstituted, mono- or poly-cyclic aliphatic, aryl, or heterocyclic systems, or (c) substituted or unsubstituted, mono-, poly-, or per-fluoro alkyl systems; the systems of (a), (b) and (c) comprising from 1 to 12 carbon atoms and 0 to 5 heteroatoms selected from O, S, N, P, and Si; and wherein $R^4$ can be connected to $R^3$ or $R^5$ to create a 5, 6 or 7 membered ring; and wherein $R^1$, $R^2$, $R^3$, $R^5$, and $R^6$ are monovalent and are selected independently from: (a), (b) and (c) described herein above, or H.

Preferably, $R^4$ is selected from: (a) substituted or unsubstituted, straight or branched, alkyl, heteroalkyl, aliphatic, heteroaliphatic, or heteroolefinic systems, (b) substituted or unsubstituted, mono- or poly-cyclic aliphatic, aryl, or heterocyclic systems, or (c) substituted or unsubstituted, mono-, poly-, or per-fluoro alkyl systems; more preferably $R^4$ is selected from (a) substituted or unsubstituted, straight or branched, alkyl, heteroalkyl, aliphatic, or heteroaliphatic systems, (b) substituted or unsubstituted, aryl, or heterocyclic systems, or (c) substituted or unsubstituted, mono-, poly-, or per-fluoro alkyl systems; more preferably substituted or unsubstituted, straight or branched, alkyl, or heteroalkyl systems.

Preferably, the $R^4$ systems of (a), (b), and (c), described herein above, comprise from 1 to 8 carbon atoms, preferably from 1 to 6, more preferably from 1 to 4 carbon atoms and from 0 to 3 heteroatoms; preferably from 0 to 2 heteroatoms; most preferably from 0 to 1 heteroatoms. Where the systems contain heteroatoms, preferably they contain 1 heteroatom. Preferred heteroatoms include O, S, and N; more preferred are O, and N; and most preferred is O.

Preferably, $R^1$, $R^2$, $R^3$, $R^4$, and $R^6$ are selected independently from any of the systems defined for $R^4$ above, and H. In alternative embodiments, any of $R^1$, $R^2$, $R^3$, $R^4$, $R^5$, and $R^6$ groups are substituted. Preferably, the substituent(s) is selected from: (a) the group of C-linked monovalent substituents consisting of: (i) substituted or unsubstituted, straight or branched, alkyl, mono- or poly-unsaturated alkyl, heteroalkyl, aliphatic, heteroaliphatic, or heteroolefinic systems, (ii) substituted or unsubstituted, mono- or poly-cyclic aliphatic, aryl, or heterocyclic systems, or (iii) substituted or unsubstituted, mono-, poly-, or per-fluoro alkyl systems; said systems of (i), (ii) and (iii) comprising from 1 to 10 carbon atoms and 0 to 5 heteroatoms selected from O, S, N, P, and Si; (b) the group of S-linked monovalent substituents consisting of $SA^1$, SCN, $SO_2A^1$, $SO_3A^1$, $SSA^1$, $SOA^1$, $SO_2NA^1A^2$, $SNA^1A^2$, and $SONA^1A^2$; (c) the group of O-linked monovalent substituents consisting of $OA^1$, OCN and $ONA^1A^2$; (d) the group of N-linked monovalent substituents consisting of $NA^1A^2$, $(NA^1A^2A^3)^+$, NC, $NA^1OA^2$, $NA^1SA^2$, NCO, NCS, $NO_2$, $N=NA^1$, $N=NOA^1$, $NA^1CN$, $NA^1NA^2A^3$; (e) the group of monovalent substituents consisting of $COOA^1$, $CON_3$, $CONA^1_2$, $CONA^1COA^2$, $C(=NA^1)NA^1A^2$, CHO, CHS, CN, NC, and X; and (f) the group consisting fluoroalkyl monovalent substituents consisting of mono-, poly-, or per-fluoro alkyl systems comprising from 1 to 12 carbon atoms and 0 to 4 heteroatoms.

For the groups (b) to (e), described above, $A^1$, $A^2$, and $A^3$ are monovalent and are independently selected from: (1) H, (2) substituted or unsubstituted, straight or branched, alkyl, mono- or poly-unsaturated alkyl, heteroalkyl, aliphatic, heteroaliphatic, or heteroolefinic systems, (3) substituted or unsubstituted, mono- or poly-cyclic aliphatic, aryl, or heterocyclic systems, or (4) substituted or unsubstituted, mono-, poly-, or per-fluoro alkyl systems; said systems of (2), (3) and (4) comprising from 1 to 10 carbon atoms and 0 to 5 heteroatoms selected from O, S, N, P, and Si; and wherein X is a halogen selected from the group consisting of F, Cl, Br, and I.

Preferred substituents for use herein include those having a Hammett Sigma Para ($\sigma_p$) Value from −0.65 to +0.75, preferably from −0.4 to +0.5. Hammett Sigma Values are described in Advanced Organic Chemistry—Reactions, Mechanisms and Structure (Jerry March, $5^{th}$ ed. (2001) at pages 368-375).

Alternative suitable radical scavengers for use herein are compounds according to the general formula (II):

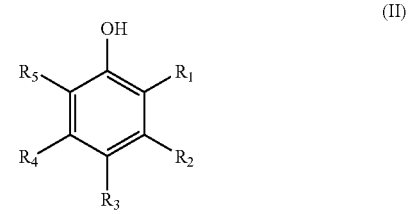

wherein $R_1$, $R_2$, $R_3$, $R_4$, and $R_5$ are each independently selected from H, $COO^-M^+$, Cl, Br, $SO_3^-M^+$, $NO_2$, $OCH_3$, OH or a $C^1$ to $C^{10}$ primary or secondary alkyl and M is either H or alkali metal. Preferably, the above-described radical scavengers have a pKa of more than 8.5 to ensure protonation of the hydroxy group.

Other suitable radical scavengers for use herein include those selected from group (III) benzylamine, imidazole, ditert-butylhydroxytoluene, hydroquinone, guanine, pyrazine, piperidine, morpholine, methylmorpholine, 2methoxyethylamine, and mixtures thereof.

Preferred radical scavengers are selected from the classes of alkanolamines, amino sugars, amino acids, esters of amino acids and mixtures thereof. Particularly preferred compounds are: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, and mixtures thereof, and the salts such as the potassium, sodium and ammonium salts thereof and mixtures thereof. Especially preferred compounds are glycine, sarcosine, lysine, serine, 2 methoxyethylamine, glucosamine, glutamic acid, morpholine, piperdine, ethylamine, 3 amino-1-propanol and mixtures thereof.

The radical scavengers preferably have a molecular weight of less than about 500, preferably less than about 300, more preferably less than about 250 in order to facilitate penetration of the radical scavenger into the hair fiber. The compositions of the present invention preferably comprise from about 0.1% to about 10% by weight, preferably from about 1% to about 7% by weight of radical scavenger. The radical scavenger is also preferably selected such that it is not an identical species as the alkalizing agent. According to one embodiment of the present invention the radical scavenger may be formed insitu in the hair dyeing compositions prior to application to the hair fibres.

In another embodiment of the present invention the kit may comprise a separate component comprising other sensitive materials such as certain dyes, for example dyes cationic azo dyes which are not stable in the main dye component.

According to the present invention the method of coloring or bleaching comprises a pre-treatment step whereby a pre-treatment composition having a viscosity from 100 Pa to 300 Pa, measured according to the method described herein, and comprising at least one conditioning agent is applied to the hair. The pre-treatment composition is worked thoroughly onto the hair to ensure even coverage of all of the hair fibers and without subsequent rinsing. A hair colorant or bleaching composition is then applied to the hair by the consumer. After working the mixture for a few minutes (to insure uniform application to all of the hair), the colorant composition or bleaching composition is allowed to remain on the hair for an amount sufficient for the dyeing to take place (usually about 30-60 minutes). The consumer then rinses his/her hair thoroughly with tap water. The consumer then optionally applies an additional conditioning composition working the composition into the hair and leaving it in the hair for 30 seconds to 10 minutes, before rinsing out with water and drying and styling the hair as usual. In another embodiment, the additional conditioner may be a leave in conditioner which is not rinsed off the hair prior to styling.

The kits described hereinabove are well known in the art and the composition in each container can be manufactured utilizing any one of the standard approaches, these include a) 'Oil in water' process, b) 'Phase Inversion' process and c) 'One-pot' process.

EXAMPLES

Pre-Treat Compositions

Compositions 4-9 below were made by heating the water to 80° C. then adding the glutamic acid and stearamidopropyl dimethylamine and fatty alcohols, EDTA and benzyl alcohol and mixing. The mixture is then cooled to below the phase transition, the additional ingredients added and then cooled to 30° C. The mixture is them milled using a Silverson SL2 for 3 minutes.

|  | Test Leg No.: | | | | | | | | |
|---|---|---|---|---|---|---|---|---|---|
|  | 1* | 2* | 3* | 4 | 5 | 6 | 7 | 8 | 9* |
| Composition | — | | | | | | | | |
| Cetyl alcohol | — | — | — | 1.05 | 2.8 | 2.45 | 1.4 | 1.75 | 1.75 |
| Stearyl alcohol | — | — | — | 1.89 | 5.04 | 4.41 | 2.52 | 3.15 | 3.15 |
| Stearamidopropyl dimethyamine | — | — | — | 0.84 | 2.24 | 1.96 | 1.12 | 1.40 | 1.40 |
| L-Glutamic acid | — | — | — | 0.27 | 0.72 | 0.63 | 0.36 | 0.45 | 0.45 |
| Tetrasodium EDTA (87%) | — | — | — | 0.03 | 0.08 | 0.07 | 0.04 | 0.05 | 0.05 |
| Benzyl alcohol | — | — | — | 0.12 | 0.32 | 0.28 | 0.16 | 0.20 | 0.20 |
| Kathon CG | — | — | — | 0.009 | 0.024 | 0.021 | 0.012 | 0.015 | 0.015 |
| silicone | — | — | — | 1.50 | 4.00 | 3.50 | 2.00 | 2.50 | 2.50 |
| Demineralised water | — | — | 100 | qs | qs | qs | qs | qs | qs |
| Rheology 850 s$^{-1}$ | — | 85 | — | 115 | 355 | 280 | 175 | 225 | 225 |

1* No pre-treatment used.

2* L'Oreal Excellence # 6 Natural Light Brown Protective Serum - pre-color care.

3* Water

9* Pre-treatment is rinsed off before color application

Pre-Treat Viscosity Measurement Protocol

An AR 500 rotational rheometer (TA Instruments Ltd., Leatherhead, Surrey KT22 7UQ, UK) is used to determine the viscosity of the pre-treatment compositions. The determination is performed at 26.7° C., with the 4 cm 2° steel cone measuring system set with a 50 μm (micron) gap and is performed via the programmed application of a shear rate from 0.5 to 1000 1/s over a 1 minute time period with 10 data points recorded per decade. These data are used to create a shear rate vs. shear stress curve for the material. The value obtained on the plotted graphs at 850 $s^{-1}$ is recorded.

The compositions were tested on a mannequin head, made from human hair, previously colored to replicate the chemical damage associated with coloring. 15 g of the pre-treatment was applied to the hair. A box of Nice' n Easy colorant shade 120 was then mixed and applied to the hair, targeting the roots, after leaving to develop for a period of time, the color was pulled through to the tip and left for a further period to develop before the colorant was then rinsed off and the hair dried.

Test legs 1, 3 and 9 (no pre-treatment, water as pre-treatment and the removal of the pre-treatment prior to colorant application) were the hardest to apply the colorant, whereas those legs using a pre-treatment (legs 2, 4, 6, 7 and 8) were all easier to apply. Leg 5 (pre-treatment having a high viscosity) also resulted in poor ease of application of the colorant. Legs 4, 6, 7 and 8 however also allowed for easy application of the colorant through the entire length of hair to the tips without tangling the hair. The pre-treatment compositions 2, 4, 5, 6, 7, 8 allowed for faster rinsing off of the colorant from the hair. Hence, from these results it is clearly demonstrated that claimed pre-treatment method results in easier and, faster colorant application, easier application of the composition from root to tip through the hair length and a faster colorant rinse.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are the scope of this invention.

What is claimed is:

1. A method of pre-treating keratinous fibres prior to the application of a hair colorant or bleaching composition comprising the steps of applying a pre-treatment composition to the keratinous fibres said composition comprising conditioning agent wherein the conditioning agent is an emulsions made from lamellar liquid crystals, where in said lamellar liquid crystals comprise:
   (a) a C16-C22 fatty alcohol;
   (b) an amidoamine of the following general formula: R22CONH($CH_2$)m N(R23)$_2$, wherein R22 is a residue of C8 to C24 fatty acids, R23 is a C1 to C4 alkyl, and m is an integer from 1 to 4;
   (c) L-glutamic acid;
and a silicone wherein said pre-treatment composition comprises from about 0.2% to about 20% of said conditioning agent.

2. A method of pre-treating keratinous fibers according to claim 1, further comprising at least one adjunct.

3. A method of pre-treating keratinous fibers according to claim 1, wherein said method comprises a further step of applying a conditioning composition after the removal of the hair coloring or bleaching composition from said fibres.

4. A method of pre-treating keratinous fibers according claim 1, wherein said hair coloring or bleaching composition comprises at least one source of a peroxymonocarbonate ions and at least one source of an alkalizing agent wherein said composition has a pH of up to and including about 9.5.

* * * * *